United States Patent [19]

Schneider

[11] Patent Number: 5,088,549
[45] Date of Patent: Feb. 18, 1992

[54] TYING NECKBAND HEAT TRANSFER DEVICE

[75] Inventor: Mark Schneider, Orlando, Fla.

[73] Assignee: Warren Locke Franz, Orlando, Fla.

[21] Appl. No.: 714,647

[22] Filed: Jun. 13, 1991

[51] Int. Cl.$^5$ ............................................. A61F 7/02
[52] U.S. Cl. ..................................... 165/46; 62/259.3; 62/530; 2/7; 128/402; 128/403
[58] Field of Search .............. 165/46; 62/259.3, 530; 2/7; 128/402, 403

[56] References Cited

U.S. PATENT DOCUMENTS

| | | | |
|---|---|---|---|
| 2,335,630 | 11/1943 | Bachardy | 2/7 |
| 2,562,121 | 7/1951 | Poux | 128/402 |
| 2,615,168 | 10/1952 | Tannenbaum | 2/197 |
| 3,696,814 | 10/1972 | Umemoto | 128/380 |
| 4,237,558 | 12/1980 | Mackenroth, III et al. | 2/181 |
| 4,277,847 | 7/1981 | Florio | 2/12 |
| 4,326,533 | 4/1982 | Henderson | 128/403 |
| 4,382,446 | 5/1983 | Truelock et al. | 128/402 |
| 4,484,363 | 11/1984 | Varanese | 2/209.1 |
| 4,551,858 | 11/1985 | Pasternack | 2/7 |
| 4,641,655 | 2/1987 | Abt | 62/259.3 |
| 4,805,619 | 2/1989 | Swearingen | 128/402 |
| 5,005,374 | 4/1991 | Spitler | 62/259.3 |

*Primary Examiner*—Albert W. Davis, Jr.
*Attorney, Agent, or Firm*—Warren L. Franz

[57] ABSTRACT

A heat transfer device in the form of a bandanna-like neckband has a main body flexible fabric material and a pocket lengthwise centrally located for receiving an elongated heat transfer element in the form of a multicellular reusable coolant pouch therein. The lengths of the main body and pocket are chosen to place the heat transfer element about the back and sides of the neck, while leaving the main body unobstructed at free ends to permit loose tying to join the ends in front of the neck. The widths of the main body and pocket are chosen to enable single or multiple layers of fabric material to be optionally interposed between the heat transfer element and the neck.

1 Claim, 2 Drawing Sheets

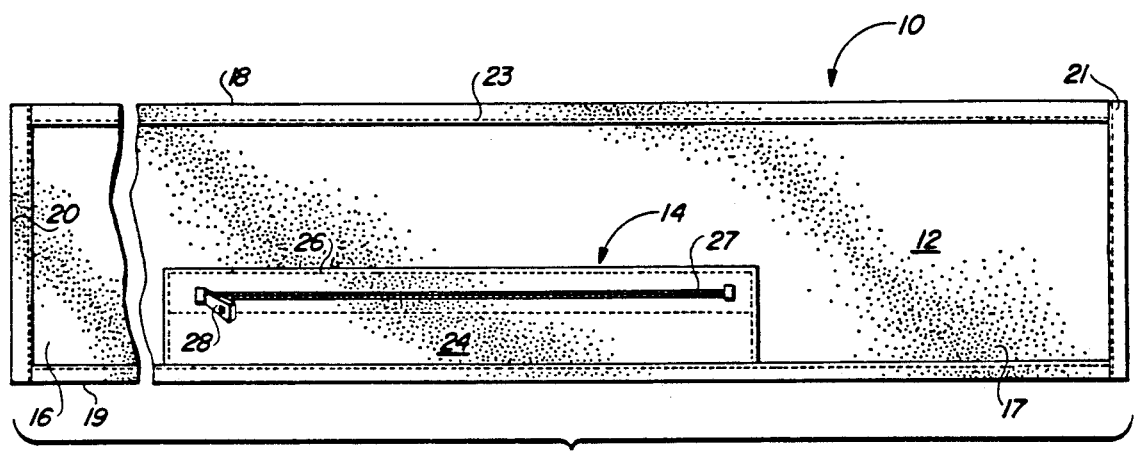
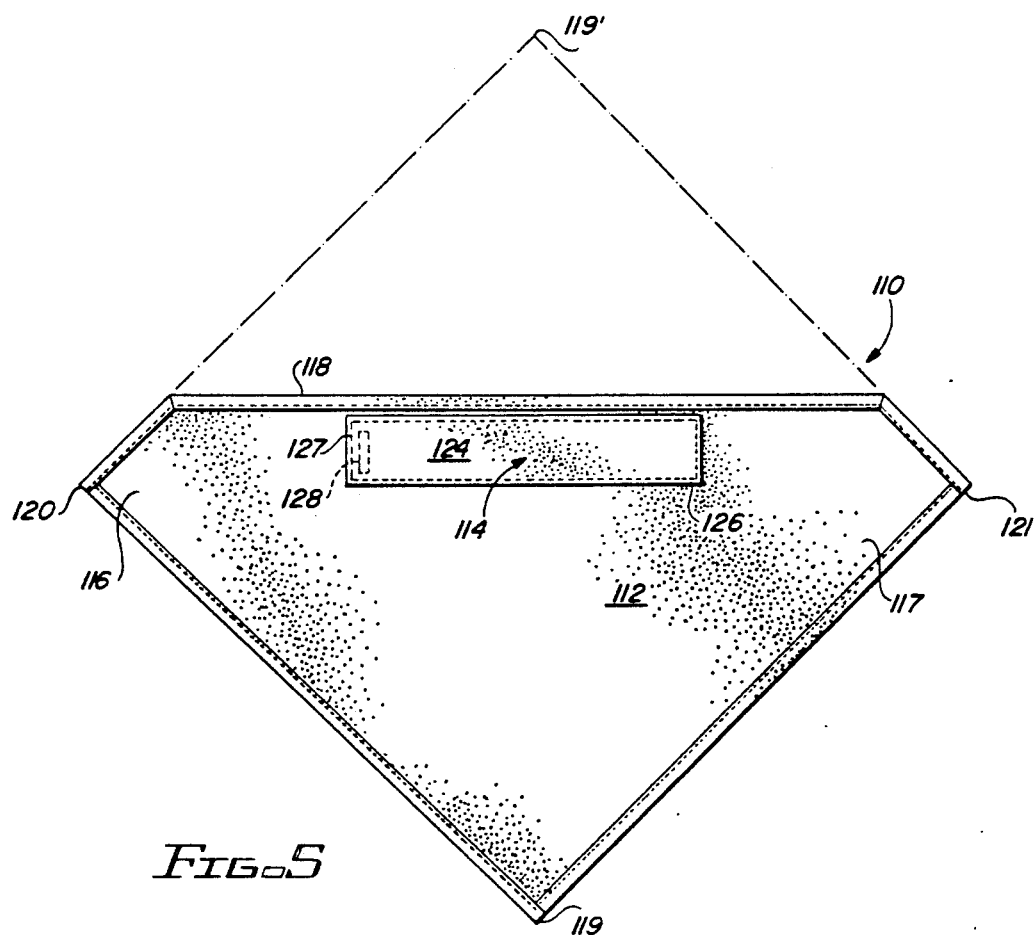

TYING NECKBAND HEAT TRANSFER DEVICE

This invention relates to a device in the form of a tying neckband or bandanna to be worn about the neck for cooling or heating the user thereof.

BACKGROUND OF THE INVENTION

It is known to employ heat transfer materials in packs to be wrapped about body parts for cooling or heating purposes. The application of hot or cold packs about the neck and face has proved effective for alleviating sore muscles, headaches, fever and similar ailments; and, in general, for increasing the overall well-being and comfort of the user. Such packs may employ water or another reusable cooling or heating medium, or may utilize a compartmentalized formulation to produce an endothermic or exothermic reaction.

A typical conventional heat transfer device of the type to which the invention relates comprises a hollow tubular neckband of single layer flexible fabric material which is wrapped circumferentially about the back and sides of a user's neck, and secured in front by means of a Velcro TM hook-and-eye or similar releasable fastener. A heat transfer element, such as a flexible liquid-tight pouch containing reusable refrigerant, is inserted in the hollow of the neckband for heat exchange with the neck through the layer of neckband material.

Such tubular neckband wraps are clumsy in appearance, giving a dog collar look that is inappropriate for social wear. The releasable fastener is uncomfortable and awkward to adjust; and no mechanism is provided for varying the thickness of neckband material lying between the heat transfer element and the user's skin.

SUMMARY OF THE INVENTION

The present invention provides a heat transfer device in the form of a bandanna-like neckband, having free ends which can be releasibly joined together by tying and having a stylish, aesthetically pleasing look. The invention further comprises a neckband heat transfer device adapted to permit variance, as desired by the use, of the number of layers of material between the heat transfer element and the skin.

The heat transfer device of the invention comprises a main body of flexible fabric material having a length and width, and a pocket lengthwise centrally located relative to the main body and into which a heat transfer element can be received. The pocket is dimensioned, configured and adapted so that the received heat transfer element received in the pocket will extend sufficiently lengthwise of the device to circumferentially envelop the back and sides of the neck, but leave sufficiently unobstructed opposite free ends lengthwise of the main body, to permit loose tying of the main body at those free ends in front of the neck. The width of the main body is chosen relative to the width of the pocket, to permit the device to be folded so that single or multiple layers of fabric material may be optionally located intermediate the heat transfer element and the skin.

In preferred embodiments, discussed in greater detail below, an elongate rectangular pocket having an opening with a releasable closure is located lengthwise centrally of a main body to extend for less than a major portion of the main body, both lengthwise and widthwise thereof. In one example, the main body portion of the device is a rectangular strip of fabric having a length and width greater than twice the length and width of the pocket, and the pocket is aligned centrally along a lower longitudinal edge of the main body. In another example, the main body has a length bounded by opposite pointed corners, and the pocket is lengthwise centrally located between the corners.

BRIEF DESCRIPTION OF THE DRAWINGS

Embodiments of the invention have been chosen for purposes of illustration and description, and are shown in the accompanying drawings, wherein:

FIG. 3 is a front plan view of the device of FIGS. 1 and 2, unfolded and laid flat;

FIG. 5 is a view, corresponding to that of FIG. 3, of a modified embodiment of the invention.

Throughout the drawings, like elements are referred to by like numerals.

DESCRIPTION OF THE PREFERRED EMBODIMENTS

The principles of the invention will be understood by reference to the examples of embodiments thereof shown in FIGS. 1-5.

Figure 1:
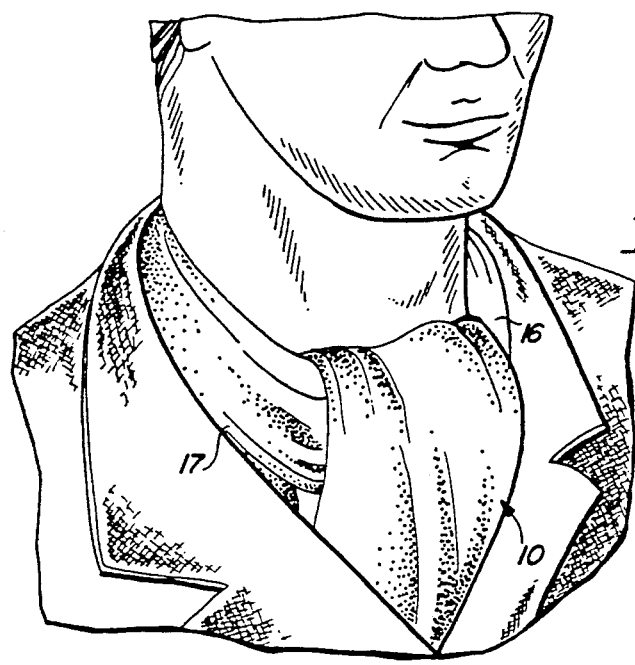
FIG. 1 is a perspective view of an embodiment of the invention shown wrapped in an aesthetically pleasing manner about the neck of a user.
Figure 2:
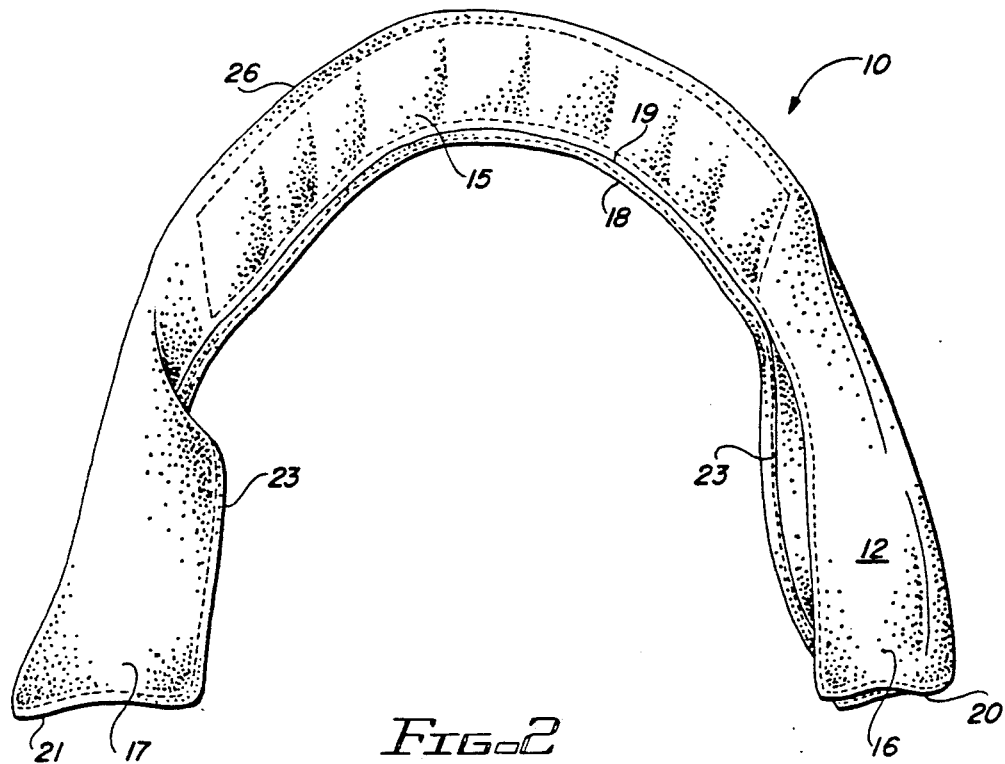
FIG. 2 is an enlarged perspective view of the device of FIG. 1, shown untied, in its orientation for positioning loosely around the neck.

A first embodiment of the invention, shown in FIGS. 1-3, takes the form of a device 10 comprising a main body 12 of flexible fabric material having a length (left to right horizontal extent in FIG. 3) and width (top to bottom vertical extent in FIG. 3), and a pocket 14 into which a heat transfer element 15 (FIG. 4) can be received in lengthwise central location relative thereto. The pocket 14 is dimensioned, configured and adapted so that the received element 15 will extend sufficiently lengthwise to circumferentially envelop the back and sides of the neck of a user, but leave left and right free ends 16, 17 of sufficient length to permit loose tying of the main body at the free ends in front of the neck, as illustrated in FIG. 1.

The main body 12, in the embodiment shown in FIGS. 1-3, comprises a generally rectangular strip of material having a length generally six times greater than its width. The material is hemmed along upper and lower longitudinal edges 18, 19 and left and right lateral edges 20, 21 by folding border portions thereof over toward the front face of the portion 12 and sewing them down along stitch lines 23. The pocket 14 is formed by applying a second generally rectangular piece 24 of the same material onto the front face of the material 12, aligned centrally along the lower edge 19. The pocket 15 is formed by joining the piece 24 to the main body 12 along border stitching lines 26.

For the shown embodiment, the piece 24 (and, thus, the resulting pocket 14) has a length just under one-half the length of the main body 12, and a width about two-fifths to one-third the width of the portion 12. Suitable dimensions for the main body 12 and pocket 14 are 32"×6" and 15"×2", respectively. An opening 27, provided in or along the edge of the material 24 to give access to the interior of the pocket 14, is fitted with a conventional releasable closure mechanism, such as the zipper 28 shown. The pocket 14 and opening 27 are dimensioned, configured and adapted to accommodate the receipt of a heat transfer element 15.

Figure 4:
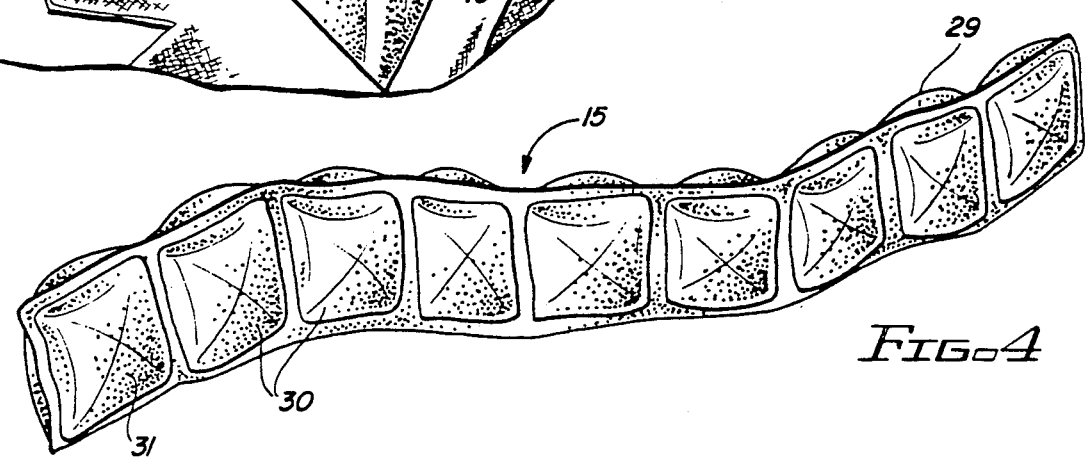
FIG. 4 is a perspective view of one form of heat transfer element insertable within the pocket of the device.

The element 15 may take the form of a multi-cellular segmented pouch 29, as shown in FIG. 4. The pouch 29 comprises a series of joined plastic film cells 30 filled with a known heat exchange substance, such as a repeatably refrigerable conventional coolant compound 31. The pouch 29 is configured to substantially match the length and width of the pocket 14, so that placement of the heat transfer element 15 will be determined by placement of the pocket 14. The pouch 29 could also be constituted by a single elongate member or a plurality of separate cells. Similarly, single-use chemical reactants could be employed in place of the reusable formulation 31.

With the device 10 utilized as a cooling neckband, the pouch 29 (FIG. 4) is placed within the pocket 14 after refrigeration, and the opening 27 closed (FIG. 3). The main body fabric 12 is then folded widthwise in half along its length (FIG. 2), bringing the upper edge 18 over and across the material 24 (as viewed in FIG. 3), and placed with the pouch 29 circumferentially positioned about the neck back and sides. The folded device 10 can be located with one layer of fabric material between element 15 and the neck, as shown in FIG. 2, to bring the left free end 16 proximate the left shoulder and the right free end 17 proximate the right shoulder. Alternatively, the device 10 may be reversed (not shown) to have two layers of material (one layer of piece 24 and one layer of piece 12) intermediate the element 15 and the neck, with the left free end 16 proximate the right shoulder and the right free end 17 proximate the left shoulder. In either orientation, the unobstructed free ends 16, 17 may be tied together in front of the neck, as shown in FIG. 1.

The stylishness of the device 10 can be enhanced by choosing bold colors and decorative prints for the fabric making up the main body 12 and pocket 14. Choice of a rayon or similar synthetic woven or knitted material provides a readily washable, comfortable device. The heat transfer element 15 can be permanently embedded in the main body 12, if desired; however, making element 15 removable for cooling or heating apart from the remainder of the device, if reusable, reduces wear and tear on the device.

FIG. 5 shows a modified embodiment of device 10 in the form of a device 110 having a length bounded by left and right pointed corners 120, 121, and a width bounded by an upper longitudinal edge 118 and a central apex 119 of an inverted triangular portion of a main body 112. A pocket 114 is formed by applying border stitching 126 along three edges of a rectangular piece of material 124. A left edge is left unstitched to form an opening 127 within which complementary parts of a Velcro TM hook-and-eye fastener are arranged to provide a releasible closure. The length of the pocket 114 and main body 112 of device 110 have the same relative dimensions as the corresponding lengths of the pocket 14 and main body 12 of device 10, discussed above. The width of the main body 112 is, however, much greater relative to the width of pocket 114, than the width of the main body 12 is to pocket 14.

The scarf-like configuration of device 110 enables the inverted triangular portion to be repeatedly overlapped about the pocket 114, if desired, to adjust the number of layers of material to be located between the heat transfer element 15 and the neck. (The position of the first overlap is suggested by the dot-dashed lines in FIG. 5, with the point 119 being brought up and over the pocket 114 to a position 119'.) Left and right free ends 116, 117, not obstructed by the coolant-filled pocket 114, can be tied at the front of the neck as with the corresponding free ends 16, 17 of device 10.

Those skilled in the art to which the invention relates will appreciate that the preferred embodiments of the invention described in detail above are just examples of how the invention can be implemented, and that various substitutions and modifications can be made to the same without departing from the spirit and scope of the invention as described by the claims below.

What is claimed is:

1. A heat transfer device for cooling or heating the neck area of a user, said device comprising:

a main body of flexible fabric material having a length and width;

a pocket of flexible fabric material, having a length, width and an interior, and being located lengthwise centrally of the length of said main body; and a heat transfer element dimensioned, configured and adapted to match said pocket interior and including a substance suitable for transferring heat to or from said neck area;

said lengths of said main body and pocket being relatively dimensioned for enabling said pocket-matching heat transfer element to be received circumferentially about the back and sides of the neck, yet leaving opposite free ends lengthwise of said main body and away from said pocket, to permit loose tying of said main body of said free ends in front of said neck; and said widths of said main body and said pocket being relatively dimensioned for permitting said main body to be folded widthwise over said pocket to permit optional user-selectable variation of the number of layers of fabric material between said heat transfer element and said neck area.

* * * * *